US006908634B2

(12) United States Patent
Hwang (10) Patent No.: US 6,908,634 B2
(45) Date of Patent: Jun. 21, 2005

(54) TRANSGLUTAMINASE SOY FISH AND MEAT PRODUCTS AND ANALOGS THEREOF

(75) Inventor: Der Chyan Hwang, Chesterfield, OH (US)

(73) Assignee: Solae, LLC, St. Louis, MO (US)

( * ) Notice: Subject to any disclaimer, the term of this patent is extended or adjusted under 35 U.S.C. 154(b) by 243 days.

(21) Appl. No.: 10/393,239

(22) Filed: Mar. 20, 2003

(65) Prior Publication Data

US 2004/0185147 A1 Sep. 23, 2004

(51) Int. Cl.[7] .................................................. A23B 7/10
(52) U.S. Cl. ........................ 426/52; 426/46; 426/656; 426/574; 435/68.1
(58) Field of Search ...................... 435/68.1; 426/52, 426/656, 46, 655, 615, 634, 574

(56) References Cited

U.S. PATENT DOCUMENTS

| | | | |
|---|---|---|---|
| 4,917,904 A | 4/1990 | Wakameda et al. ............ 426/7 |
| 5,037,664 A | 8/1991 | Kyogoku et al. ............ 426/573 |
| 5,055,310 A | 10/1991 | Nonaka et al. ............... 426/46 |
| 5,082,672 A | 1/1992 | Hamada et al. ................ 426/7 |
| 5,093,028 A | 3/1992 | Kyogoku et al. ......... 252/315.1 |
| 5,098,733 A | 3/1992 | Kyogoku et al. ............ 426/573 |
| 5,156,956 A | 10/1992 | Motoki et al. ............. 435/68.1 |
| 5,182,130 A | 1/1993 | Haralampu et al. ............ 427/3 |
| 5,279,839 A | 1/1994 | Gottmann et al. ............ 426/20 |
| 5,518,742 A | 5/1996 | Soeda et al. ................. 426/63 |
| 5,658,605 A | 8/1997 | Soeda et al. .................... 426/7 |
| 5,670,192 A | 9/1997 | Budolfsen et al. ............ 426/34 |
| 5,681,598 A | 10/1997 | Kuraishi et al. .............. 426/36 |
| 5,698,245 A | 12/1997 | Tanaka et al. ................ 426/10 |
| 5,707,668 A | 1/1998 | Andersen ..................... 426/42 |
| 5,731,183 A | 3/1998 | Kobayashi et al. ......... 435/193 |
| 5,834,232 A | 11/1998 | Bishop et al. ............. 435/68.1 |
| 5,858,423 A | 1/1999 | Yajima et al. .................. 426/3 |
| 5,866,180 A | 2/1999 | Budolfsen et al. ............ 426/42 |
| 5,907,031 A | 5/1999 | Soeda et al. ................ 530/350 |
| 5,965,176 A | 10/1999 | Yamamoto ................... 426/46 |
| 5,968,568 A | 10/1999 | Kuraishi et al. .............. 426/56 |
| 6,190,879 B1 | 2/2001 | Bech et al. ................ 435/68.1 |
| 6,258,390 B1 | 7/2001 | Budtz ......................... 426/36 |
| 6,303,162 B1 * | 10/2001 | Susa et al. .................... 426/56 |
| 6,383,533 B1 | 5/2002 | Soeda et al. .................. 426/56 |
| 6,416,797 B1 | 7/2002 | Han et al. ..................... 426/36 |
| 6,420,148 B2 | 7/2002 | Yamaguchi ................. 435/189 |
| 6,491,957 B2 * | 12/2002 | Terazaki et al. .............. 426/94 |
| 6,495,187 B1 | 12/2002 | Borders et al. ............. 426/582 |
| 6,528,100 B1 * | 3/2003 | Hoff et al. ..................... 426/2 |
| 6,582,739 B1 * | 6/2003 | Sawano et al. ............... 426/46 |

FOREIGN PATENT DOCUMENTS

| | | | |
|---|---|---|---|
| JP | 58-149645 | 9/1983 | |
| JP | 02-257831 | 10/1990 | |
| JP | 07-227217 | * 8/1995 | ............. A23J/3/16 |
| JP | 2000-050844 | * 2/2000 | ........... A23C/1/317 |
| RU | 369013 | * 1/1995 | ............. A23J/0/00 |
| WO | 93/22930 | * 11/1993 | ........... A23C/11/00 |

\* cited by examiner

*Primary Examiner*—Keith Hendricks
(74) *Attorney, Agent, or Firm*—Richard B. Taylor (57) ABSTRACT

This invention relates to a transglutaminase-coupled vegetable protein composition and a process for preparing said composition. Further, this invention relates to soy fish and meat products and analogs thereof and a process for making the same.

22 Claims, 4 Drawing Sheets

TRANSGLUTAMINASE SOY FISH AND MEAT PRODUCTS AND ANALOGS THEREOF

FIELD OF THE INVENTION

This invention relates to soy fish and meat products and analogs thereof and a process for making the same. The soy meat and fish product and its analogs are a protein composition formed by the glutamine and lysine residues in soy protein with a cross-linking agent of a transglutaminase. The composition so formed is a controlled salt sensitive epsilon-(gamma-glutamine)-lysine crossed-linked protein.

BACKGROUND OF THE INVENTION

Protein compositions are used in the food industry in a variety of applications. However, compositions made by a transglutaminase process wherein salt sensitivity is controlled have never before been appreciated.

U.S. Pat. No. 5,055,310 (Nonaka et al., Oct. 8, 1991) relates to a shelf stable soybean curd which is stable for extended periods of time and is prepared by reacting soy milk with a solidifying agent and transglutaminase, which is not dependent on $Ca^{+2}$ ions and which is capable of catalyzing the acyl rearrangement of γ-carboxyamide in the glutamine residue of a peptide chain at a temperature not higher than 80° C. to prepare a soybean curd in a heat-resistant container, and retorting the package soybean curd.

U.S. Pat. No. 5,156,956 (Motoki et al., Oct. 20, 1992) relates to transglutaminase catalyzing an acyl transfer reaction of a γ-carboxyamide group of a glutamine residue in a peptide or protein chain in the absence of $Ca^{2+}$ and to a process for producing a protein gelation product using transglutaminase. Transglutaminase catalyzes an acyl transfer reaction of a γ-carboxyamide group of a glutamine residue in a peptide chain. The transglutaminases form intramolecular or intermolecular ε-(γ-Glu)-Lys cross-linking wherein the ε-amino group of the lysine residue in the protein serves as the acyl receptor. The gelation products of this reference produced utilizing transglutaminases are used as yogurt, jelly, cheese, gel cosmetics, etc., including conventional gel foodstuffs and gel cosmetics.

U.S. Pat. No. 6,416,797 B1 (Han et al., Jul. 9, 2002) includes a process for making cream cheese wherein nutrients typically lost as whey during processing are utilized in the final cream cheese, the resulting cream cheese has the body, texture and taste of conventional cream cheese. The process of this reference utilizes acidifying and cross-linking steps to process a dairy liquid into a wheyless cream cheese by utilizing the protein cross-linking activity of transglutaminase. The wheyless cream cheese does not require the addition of stabilizers and/or emulsifiers.

U.S. Pat. No. 6,420,148 B2 (Yamaguchi, Jul. 16, 2002) relates to a method for cross-linking a protein using an enzyme and more particularly, it relates to a method for cross-linking protein using a multi-copper oxidase such as laccase or bilirubin oxidase.

Japanese Patent Publication No. 02-257831A (Takahiko et al., Publication Date Oct. 18, 1990) relates to the manufacturing method for vegetable protein powders whose quality is enhanced by transglutaminase treatment, and that of tofu made from vegetable protein powders.

SUMMARY OF THE INVENTION

This invention relates to a transglutaminase-coupled vegetable protein composition and a process for preparing said composition. Further, this invention relates to soy meat and fish analog products prepared by the process of this invention.

DETAILED DESCRIPTION OF THE INVENTION

This invention is directed to a transglutaminase-cross-linked vegetable protein composition that has a controlled salt sensitivity and a process for preparing the composition. The composition has utility in fish and meat products or in a meat analog product. These products all contain salt and it thus becomes important to have a transglutaminase cross-linked vegetable protein composition with an acceptable or controlled salt sensitivity. The transglutaminase cross-linking is the bringing together of the glutamine and lysine residue in protein as per the following equation, wherein TG signifies transglutaminase:

The starting material for the composition of this invention is a vegetable protein extract. The vegetable protein extract may be obtained using conventional processes. Typically, soybeans are first washed to remove dirt and small stones and screened to remove damaged beans and foreign materials. The cleaned raw soybeans are then cracked into several pieces, typically six to eight, to produce soy chips and hulls. The hulls are removed by aspiration. Alternatively, the hulls may be loosened by adjusting the moisture level and mildly heating the soybeans before cracking. Hulls can also be removed by passing cracked pieces through corrugated rolls revolving at different speeds. In these methods, the hulls are removed by a combination of shaker screens and aspiration. The soy chips, which typically contain about 11% moisture, are then conditioned at about 60° C. and flaked to a thickness of about 0.25 millimeters. The resulting flakes are then extracted with an inert solvent, such as a hydrocarbon solvent, typically hexane, to remove the soybean oil. The flakes are typically desolventized in a manner which minimizes the amount of cooking or toasting of the protein to preserve a high content of water-soluble protein. The industry typically uses vapor desolventizers or flash desolventizers. The resulting defatted flakes have a protein content of approximately 50%. Any residual solvent may be removed by heat and vacuum. The defatted flakes are then milled, usually in an open-loop grinding system, by a hammer mill, classifier mill, roller mill or impact pin mill into flours or grits with desired particle sizes. Screening is typically used to size the product to uniform particle-sized ranges, and can be accomplished with shaker screens or cylindrical centrifugal screeners. Vegetable protein is extracted from the milled, defatted flakes with water, that is, without a pH adjustment. Alternatively, the vegetable protein is extracted from the milled, defatted flakes at a pH of from about 6 up to about 11 and preferably up to about 10, by the addition of acid or of base. The extract enters a first centrifuge to separate the soluble fraction from the insoluble fibrous residue. The insoluble fibrous residue may be subjected to a second extraction and second centrifugation. The extracts are then combined. The result is a clarified soy protein extract.

Before being treated with transglutaminase, the soy protein extract is heated to a temperature at which transglutaminase will be active in the catalysis of an acyl transfer reaction of a gamma-carboxyamide group of a glutamine residue in a peptide chain of the soy protein in the extract. A desirable temperature is in the range from about 40° C. to about 60° C., with a preferred temperature being about 50° C. Below about 40° C., the acyl transfer reaction proceeds at an undesirably low rate, and above 60° C., excessive denaturation of the protein can occur. The starting soy protein extract desirably has a solids content less than 6%, and preferably in the range from about 3% to about 5%.

After the pH and temperature of the protein extract have been properly adjusted, transglutaminase is added in an amount sufficient to effect the acyl transfer reaction. The amount of transglutaminase added to the soy protein extract depends to an extent on the activity of the transglutaminase. Measurement of the activity of transglutaminase may be carried out by performing a reaction using benzyloxycarbonyl-L-glutaminyl glycine and hydroxylamine as substrates in the absence of calcium ions, forming an ion complex with the resulting hydroxamic acid in the presence of trichloroacetic acid, measuring absorption at 525 nanometers and determining the amount of hydroxamic acid by a calibration curved to calculate the activity. First, a Reagent A is prepared by combining 0.2M trishydrochloride buffer (pH 6.0) 0.1M hydroxylamine, 0.01M reductive glutathione and 0.03M benzyloxycarbonyl L-glutaminyl glycine. A Reagent B is made of equal volumes of 3N hydrochloric acid, 12% trichloroacetic acid, and 5% $FeCl_3 \cdot 6H_2O$ (dissolved in 0.1N hydrochloric acid). To 0.05 ml of an enzyme solution is added 0.5 ml of Reagent A. After reacting the enzyme solution with Reagent A at 37° C. for 30 minutes, Reagent B is added thereto to discontinue the reaction and form an ion complex. Thereafter, absorbence is measured at 525 nanometers. As a control, absorbence is measured after reacting a previously thermally inactivated enzyme solution with Reagent A and terminating the reaction with Reagent B in a similar manner, and a difference is absorbence between the control and the enzyme solution is measured. Separately, a calibration curve is prepared using L-glutamic acid and gamma-monohydroxyamino acid instead of the enzyme solution, and the amount of hydroxamic acid produced is determined by the difference in absorbence described above. An enzyme activity which produces one micromol ($10^{-3}$ mol) of hydroxamic acid per minute is defined as one unit. A suitable transglutaminase derived from microorganisms in accordance with the teachings of U.S. Pat. No. 5,156,956 is commercially available. These commercially available transglutaminases typically have an enzyme activity of about 100 units. The amount of transglutaminase (having an activity of about 100 units) added to the soy protein extract is expressed as a transglutaminase concentration which is the units of transglutaminase per 100 grams of extracted solid. The extract contains from 58% to 72% protein and preferably from 62% to 68% protein. The transglutaminase concentration is at least 0.15, preferably 0.25 and most preferably 0.30 units transglutaminase per gram protein up to 0.80 and preferably 0.65 units transglutaminase per gram protein. Higher and lower amounts may be used. However, amounts below about 0.15 units transglutaminase per gram protein are less economical because of slow reaction rates, and amounts above 0.80 units transglutaminase per gram protein are uneconomical due to the relatively high cost of the transglutaminase.

The reaction is allowed to proceed for a time sufficient to achieve partial cross-linking of the soy protein in the extract, but not so long as to permit gelation of the protein. The appropriate reaction time depends on the activity and concentration of the transglutaminase, the protein concentration, and the temperature at which the protein extract is maintained during reaction. An appropriate reaction time can be determined experimentally for a given set of reaction conditions (e.g., reaction temperature, transglutaminase activity, transglutaminase concentration, the particular vegetable protein extract, and the solids content of the extract). An appropriate reaction time may then be selected to ensure that gel formation does not occur as a result of the transglutaminase catalyzed acyl transfer reaction. A suitable reaction time is from about 10 minutes to about 60 minutes and preferably from about 20 to about 50 minutes. For example, a suitable extent of cross-linking of a soy protein extract having a solids content of about 5%, a transglutaminase concentration of about 0.3 units transglutaminase per gram protein based on the total weight of the extract and reaction temperature of about 50° C. is from about 30 to 50 minutes.

When the reaction is considered over, the partially cross-linked soy protein is acid-precipitated. Acid precipitation may be achieved by adding a suitable food grade acid such as hydrochloric acid to the reaction product to adjust the pH of the mixture to the isoelectric point of the protein (e.g., about 4.5). The addition of the food grade acid to a pH of less than 5 causes the transglutaminase to be less active.

The acidic partially cross-linked soy protein mixture is then water washed, water diluted and centrifuged to remove the transglutaminase and the pH is adjusted to about 7 by adding an appropriate amount of aqueous sodium hydroxide. The partially cross-linked soy protein mixture is then subjected to a sterilization or pasteurization step by heating the partially cross-linked soy protein mixture at a relatively high temperature for a short period of time. This pasteurization step kills microorganisms in the mixture. For example, an effective treatment for killing microorganisms in the mixture involves heating the partially cross-linked soy protein mixture to a temperature of about 265° F. (about 130° C.) for about 10 seconds. A temperature of 265° F. is used to ensure the killing of microorganisms. While a temperature lower than 265° F. may work, a temperature of at least 265° F. provides a safety factor. Temperatures greater than 300° F. also have an effect on the killing of microorganisms. Typically an upper temperature associated with pasteurization is 400° F., preferably 350° F. and most preferably 310° F. However, the cost associated with the higher temperature does not translate to a product that contains appreciably fewer harmful microorganisms. In practicing this invention, the partially cross-linked soy protein mixture before pasteurization, generally has a percent solids of from 8–11.5%, preferably from 9–10.5% and most preferably from 9–10%.

The precipitated, partially cross-linked protein is preferably dried to form a powdered protein material which rapidly gels when added to water. Drying is carried out by spray drying. The partially cross-linked soy protein mixture is sprayed into a dryer at an inlet temperature of from 400–550° F., preferably 450–500° F. The outlet temperature for spray drying is from 150–250° F. and preferably at about 200° F.

The salt sensitive vegetable proteins of this invention are characterized by the presence of epsilon-(gamma-glutamine)-lysine cross-links which are formed during treatment with transglutaminase. The extent of the partial cross-linking is sufficient to form a modified vegetable protein having unique gelling thickening properties, but less than is needed to form a gel.

The invention having been generally described above, may be better understood by reference to the examples described below.

EXAMPLE 1

A transglutaminase coupled soy protein was prepared wherein 0.3 units transglutaminase per gram protein was utilized for coupling with a 30 minute hold and pasteurization at 10.2% total solids.

Figure 1:
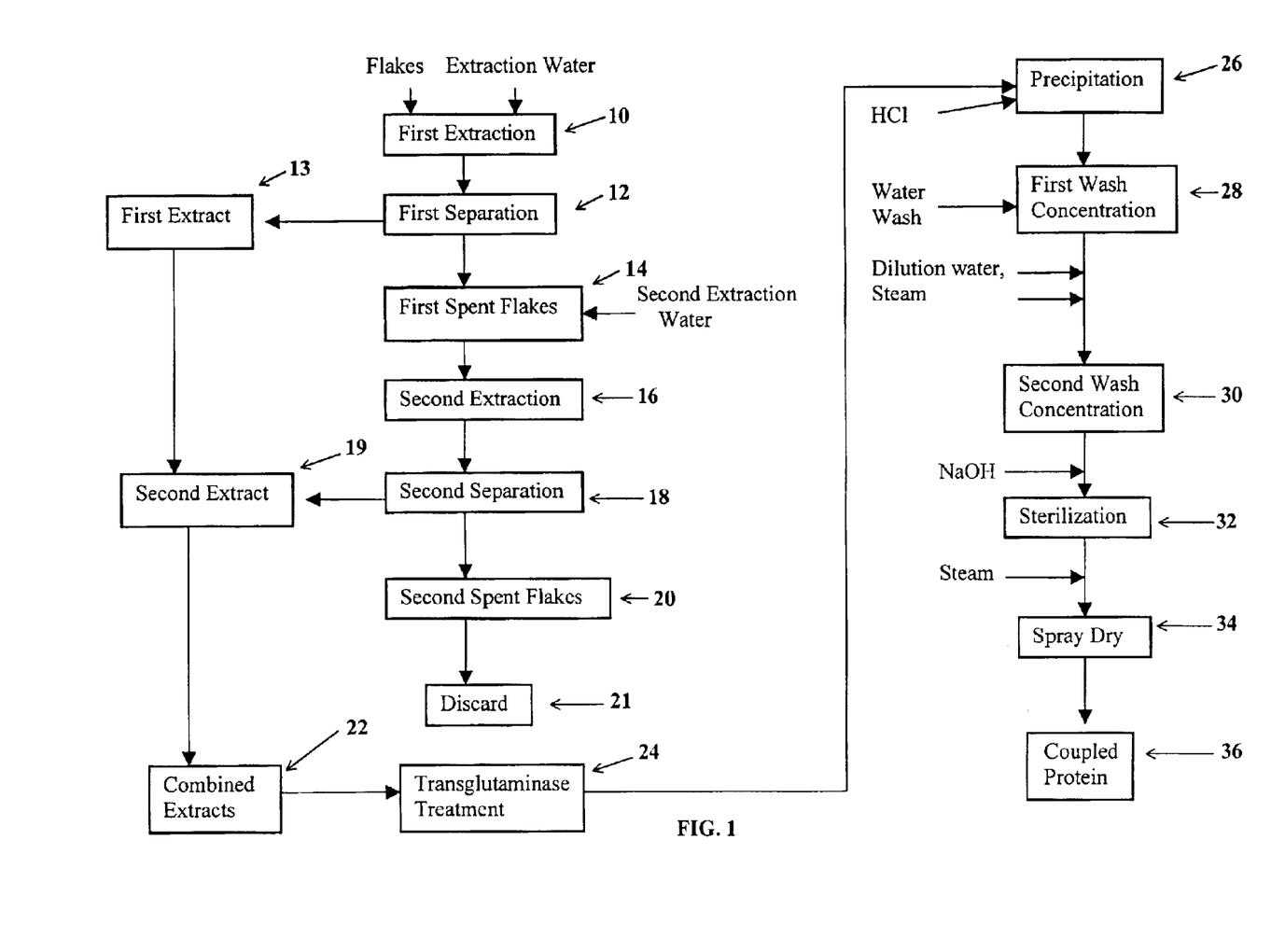
FIG. 1 is a block flow diagram of a process for producing a transglutaminase-cross-linked vegetable protein in accordance with the principles of the invention.

An extract was prepared using a standard two-stage co-current extraction process. Soy flour and water at a ratio of 1 part flour and 10 parts water are introduced into the first extraction 10. The first extraction pH was as-is with no chemical adjustment. The first extraction slurry at a total solids of 8.5% was pumped to the first separation 12 at a rate of 116 pounds a minute and separated in a centrifugal separator at a bowl speed of 4000 RPM (revolutions per minute) and a pinion speed of 3000 RPM. The first extract 13, at a total solids of 6.7% was pumped to a combined extract line while the first spent flakes 14 at a total solids of 21.4% were reslurried with 60 pounds of water to give a total solids of 4.4% and a second extraction performed at 16 and pumped to 18. At 18, there was a second separation in a centrifugal separator at a bowl speed of 4000 RPM and a pinion speed of 3000 RPM to give a second extract 19 at a total solids of 1.6% which is added to the combined extract line at 22. The second spent flakes 20 are discarded at 21. The combined extract at 22 had a 4.9% total solids. It was heated to 122° F. and 24 grams transglutaminase at a solids of 30% was added and held for 30 minutes. The transglutaminase treated extract at 24, at a total solids of 4.8% was pumped to a precipitation tank 26 at a rate of 162 pounds a minute and precipitated to pH 4.45±0.05 using 37% aqueous HCl. As the precipitate, at a total solids of 4.6% was pumped to 28, 30 pounds of wash water was added, the precipitate centrifuged and 55 pounds a minute of dilution water was added to the underflow. The overflow, which contained the transglutaminase, at 2.2% total solids was discarded and the underflow at a 7.9% total solids was pumped to 30 at a temperature of 135° F. and diluted. The diluted underflow at 3.6% total solids was concentrated using a bowl speed of 4000 RPM and a pinion speed of 3000 RPM. Whey, at a 1.7% total solids was discarded and the concentrated curd cake, at a 43.2% total solids was diluted with 0.79 gallons of water a minute to a total solids of 24.6% and was then ground, chilled and stored at a temperature of less than 40° F. for further processing.

This concentrated cake was diluted with water to give a diluted curd having 10.2% total solids. The pH of this mixture was adjusted from 4.55 to 7.22 by the addition of 50% aqueous sodium hydroxide. The pH adjusted material at 10.2% total solids was pasteurized at a temperature of at least 262° F. for 9 seconds. The material was then flash cooled to 132° F. The flash cooled material at 9.6% total solids was pumped to 34 at an inlet temperature of 443° F. and an exhaust temperature of 199° F. and spray dried to produce the coupled protein at 36.

EXAMPLES 2–5

But for minor variations, the procedure of Example 1 was repeated except for the solids content at pasteurization as noted below.

| Example | Solids |
| --- | --- |
| 2 | 10.9% |
| 3 | 11.4 |
| 4 | 11.1 |
| 5 | 11.8 |

EXAMPLES 6–10

But for minor variations, the procedure of Example 1 was repeated except that the concentration of transglutaminase was changed from 0.3 to 0.6 units transglutaminase per gram protein and that the solids content at pasteurization is as noted below.

| Example | Solids |
| --- | --- |
| 6 | 9.4% |
| 7 | 10.1 |
| 8 | 10.2 |
| 9 | 10.6 |
| 10 | 10.4 |

It has been observed that there is a correlation of gel strengths, both with and without the addition of salt to the transglutaminase cross-linked vegetable protein. This correlation revolves around the amount of solids present when pasteurization is conducted. While a positive salt sensitivity value is most desired, a negative salt sensitivity value is acceptable so long as the negative value is not greater than −30%. A "controlled salt sensitivity" means that the salt sensitivity will range from −30% to +30% and most preferably from 0 to +20%. When the solids are greater than 11.5% prior to pasteurization, the salt sensitivity is greater than −30%. At a solids content of below 10.5%, the salt sensitivity is a positive value. This gel strength, both with and without the addition of salt, is determined by the procedure as discussed below. Salt sensitivity is the % change in the gel strength of the protein by the addition of 2% by weight of salt (NaCl) to the protein. The calculation of salt sensitivity is indicated below wherein Gŝ signifies gel strength without salt and Gĉ signifies gel strength with the addition of 2% salt. The object is to have the gel strength of a protein containing salt to be equal to or greater than the get strength of a protein without salt.

Salt Sensitivity=(Gĉ−Gŝ)/Gŝ×100

Salt is present in emulsified foods such as fish, meat or meat analog products that contain vegetable proteins. Salt sensitivity thus becomes a screening test or tool for evaluating vegetable proteins. The controlled salt sensitivity of a vegetable protein that contains 2% salt is indicative of the feasibility of the emulsified food that contains vegetable proteins.

To determine gel strength, a protein mixture is prepared. One part protein powder, with or without salt, is dissolved in 6 parts of water, mixed and boiled for a period of time sufficient to permit the formation of a gel. A three piece 307 by 113 millimeters aluminum can is filled with the gel and the can is sealed. The can is placed in a boiling water bath for 30 minutes. The can is removed from the boiling water bath and cooled under a stream of tap water at 27° C.±5° C. The can is stored in a refrigerator for 16–24 hours at a temperature of −5° C. to 5° C. The can is opened and the gel is separated from the can, leaving the gel sitting on the can bottom. The strength of the gel is measured with an instrument which drives a probe into the gel until the gel breaks and measures the break point of the gel (preferably an Instron Universal Testing Instrument Model No. 1122 with 36 mm disk probe). The gel strength is calculated from the recorded break point of the gel. The calculation of the gel strength is made according to the following formula: Gel Strength (grams)=(454)(Full Scale Load of the instrument required to break the gel) times (recorded break point of the gel (in instrument chart units out of a possible 100 chart units))/100.

Figure 2:
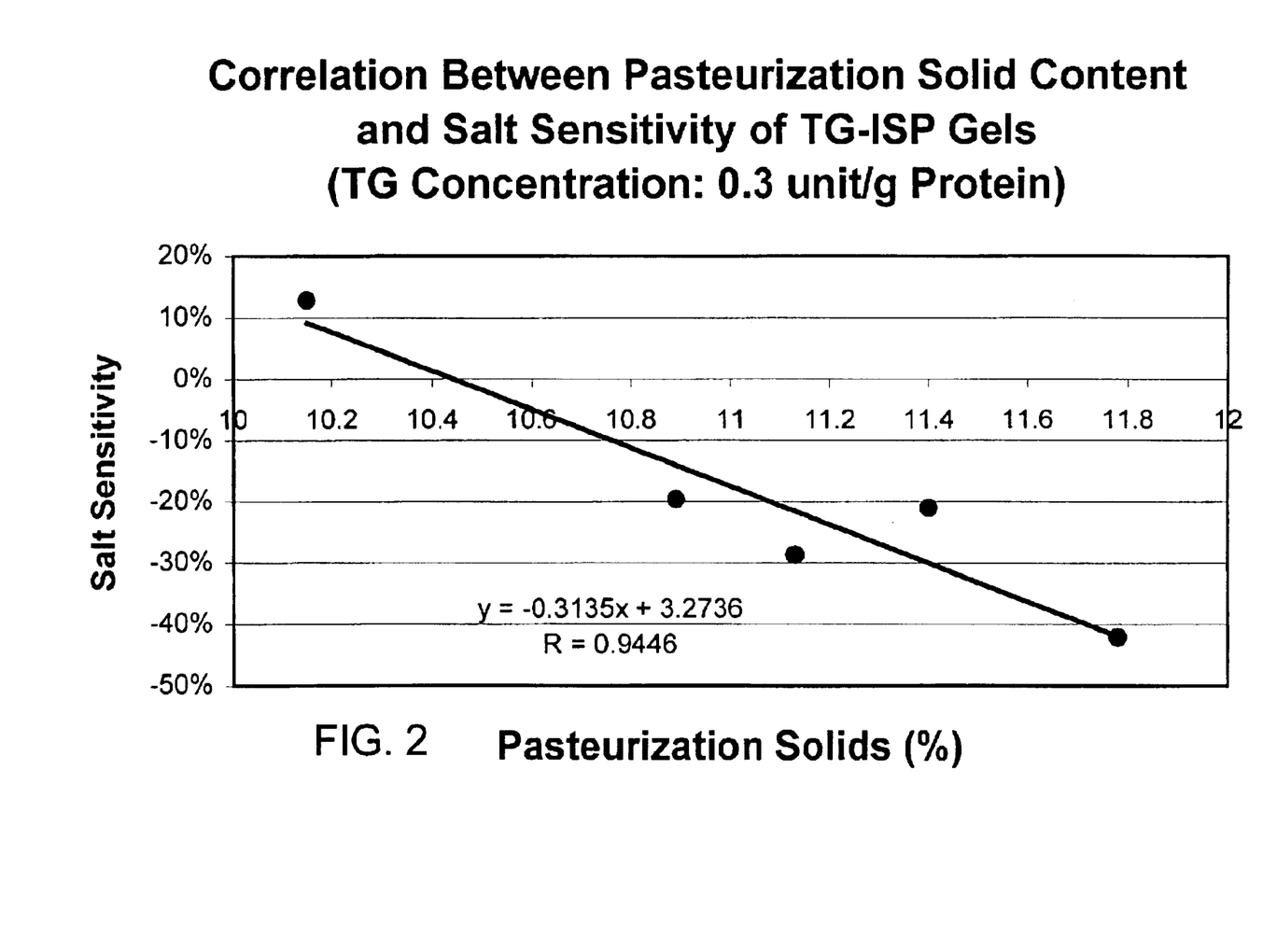
FIG. 2 is a chart representation of a transglutaminase coupled protein of the invention wherein the transglutaminase concentration is 0.3 units transglutaminase per gram protein having a solid content at pasteurization of at least 265° F. for 9 seconds and the % change in pasteurized gel strength when 2% salt is added to the coupled protein.

The data in Table I becomes the basis for the chart of FIG. 2. Table I relates to a coupled protein using 0.3 units transglutaminase per gram soy protein. The solids content at pasteurization fairly correlates to the value of the salt sensitivity. When the solids content is greater than 11.5% at pasteurization, the value of the salt sensitivity (the % change in gel strength with the addition of 2% salt) is a value greater than −30% and thus not acceptable. The curve in FIG. 2 shows that the 0% salt sensitivity occurs when the solids prior to pasteurization are preferably below 10.4%.

TABLE I

Pasteurization Solids for 0.3 Units
Transglutaminase per Gram Soy Protein

| Example | Solids | Gĉ | Gŝ | Salt Sensitivity % |
|---|---|---|---|---|
| 1 | 10.2% | 4268 | 3780 | 12.9 |
| 2 | 10.6 | 3258 | 4053 | −19.6 |
| 3 | 11.4 | 3382 | 4283 | −21.0 |
| 4 | 11.1 | 4029 | 5652 | −28.7 |
| 5 | 11.8 | 2566 | 4421 | −42.1 |

Figure 3:
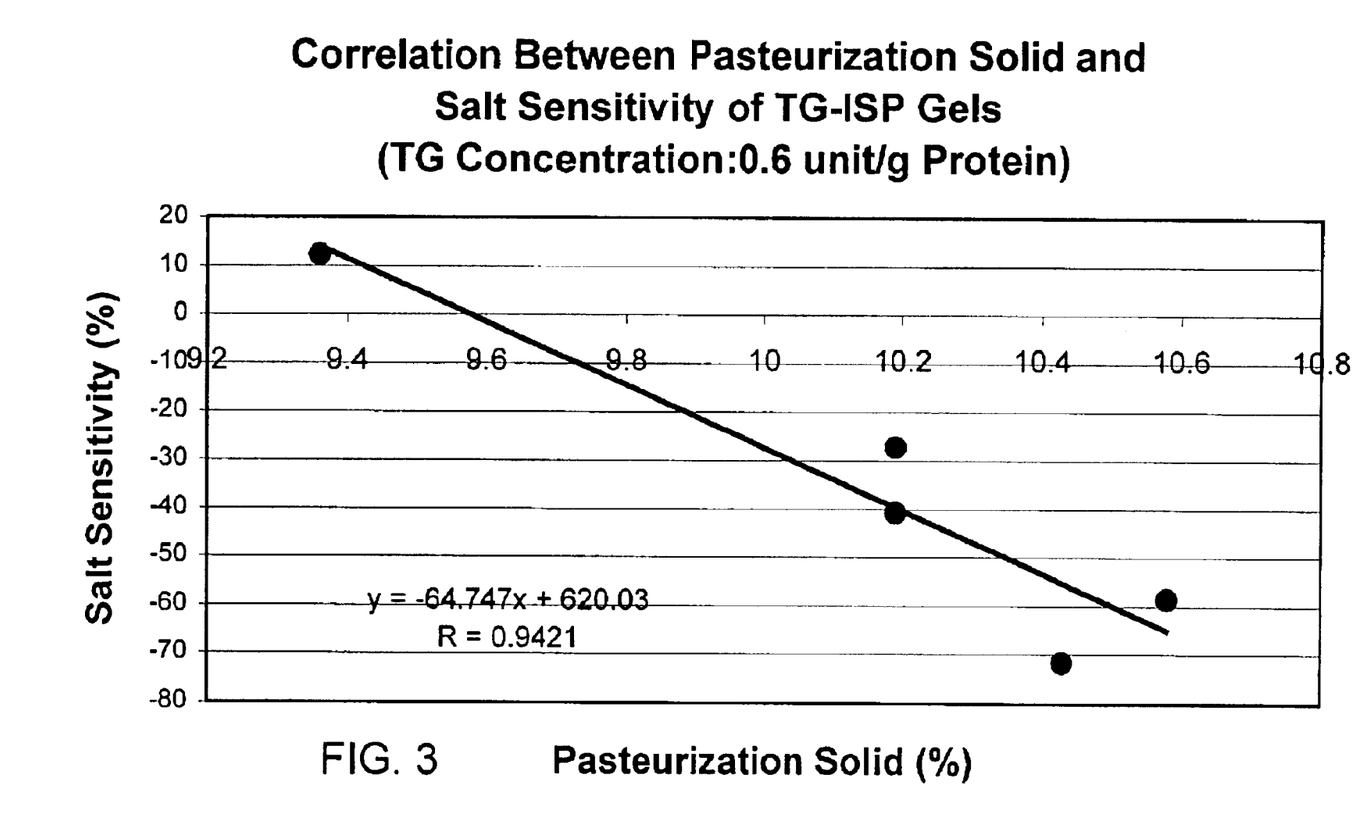
FIG. 3 is a chart representation of a transglutaminase coupled protein of the invention wherein the transglutaminase concentration is 0.6 units transglutaminase per gram protein having a solid content at pasteurization of at least 265° F. for 9 seconds and the % change in gel strength when 2% salt is added to the coupled protein.

The data in Table II becomes the basis for the chart of FIG. 3. Table II relates to a coupled protein using 0.6 units transglutaminase per gram isolated soy protein. The solids content at pasteurization fairly correlates to the value of the salt sensitivity. When the solids content is greater than about 10.2% at pasteurization, the value of the salt sensitivity (the % change in gel strength with the addition of 2% salt) is a value greater than −30% and thus not acceptable. The curve in FIG. 3 shows that the 0% salt sensitivity occurs when the solids prior to pasteurization are preferably at about 9.6%.

TABLE II

Pasteurization Solids for 0.6 Units
Transglutaminase per Gram Soy Protein

| Example | Solids | Gĉ | Gŝ | Salt Sensitivity % |
|---|---|---|---|---|
| 6 | 9.4% | 3723 | 3314 | 12.3 |
| 7 | 10.1 | 3156 | 4336 | −27.2 |
| 8 | 10.2 | 4011 | 6769 | −40.7 |
| 9 | 10.6 | 4011 | 8842 | −58.6 |
| 10 | 10.4 | 1860 | 6563 | −72.0 |

Figure 4:
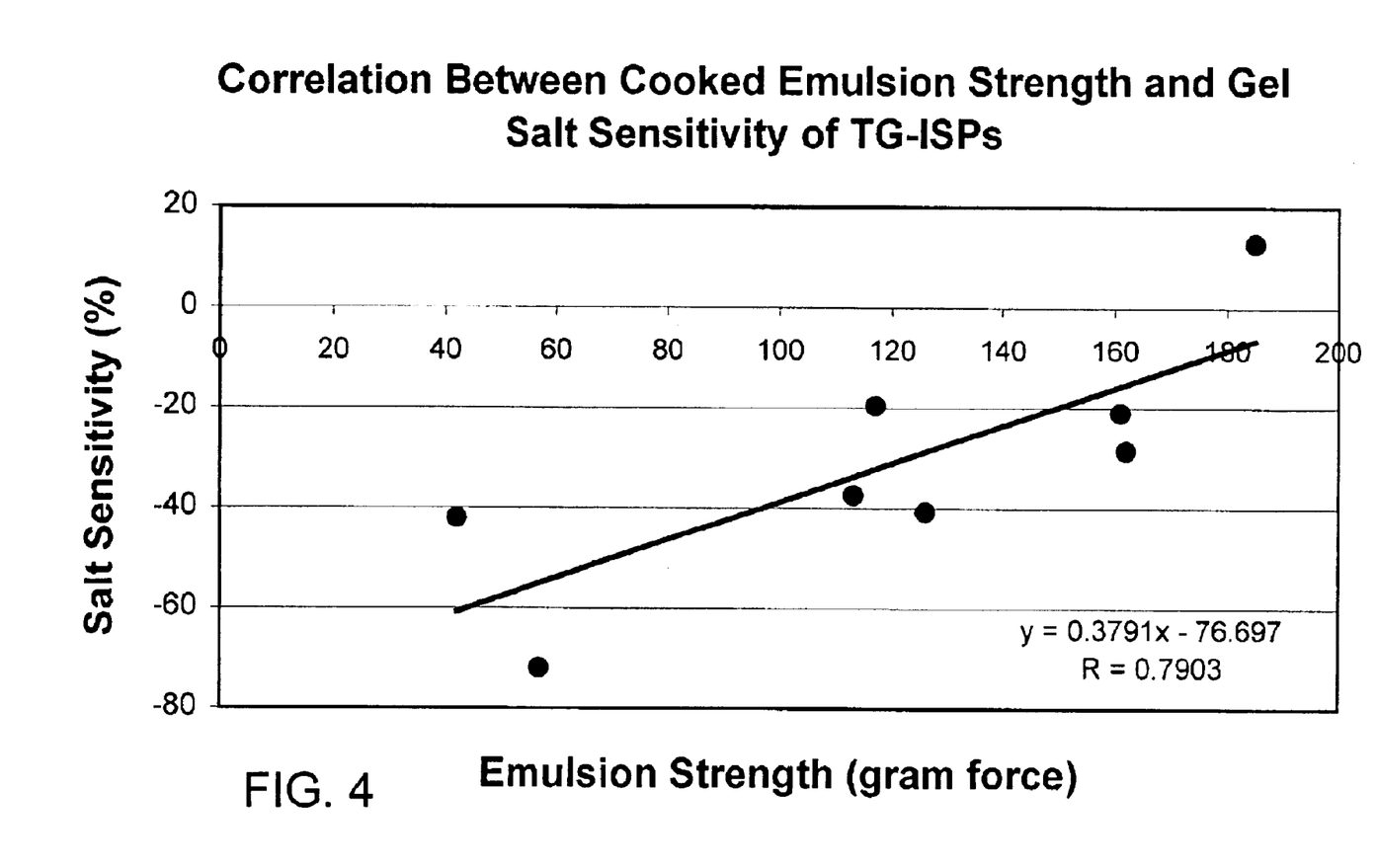
FIG. 4 is a chart representation of the cooked emulsion strength versus the % change in pasteurized gel strength of a transglutaminase coupled protein when 2% salt is added.

FIG. 4 relates to the correlation of salt sensitivity and cooked emulsion strength. As discussed earlier, the salt sensitivity is the % change in the gel strength of the protein by the addition of 2% salt. The cooked emulsion strength is expressed in grams force of a protein composition of the transglutaminase cross-linked vegetable protein, water and oil in a weight ratio of 1.0:5.75:4.2, further wherein this protein mixture is boiled for 30 minutes. The emulsion strength of the transglutaminase cross-linked vegetable protein is directly related to its performance in an emulsified meat application. That is, the higher the emulsion strength of the transglutaminase cross-linked vegetable protein, the better the texture of a meat product that contains the transglutaminase cross-linked vegetable protein. From FIG. 4 it is observed that the higher the salt sensitivity (the % change in gel strength), the higher the emulsion strength of the protein. A cooked emulsion strength of 115 grams force for the above weight ratio protein composition has been determined as the minimum value to warrant a good performance in an emulsified meat application. Based on a curve drawn to fit the data generated, it is recognized that an emulsion strength of at least 115 grams force corresponds to a salt sensitivity of at less than −30%.

This invention also relates to fabricated fish, meat and meat analog products and particularly such products which are fabricated into the form of chunks. The fabricated fish, meat and meat analog products are made from the composition of this invention as well as the process for producing the composition of this invention and are advantageously used as foods for human consumption.

The composition and process of this invention also comprise the steps of reducing the size of fish, meat and meat analog products, such as by grinding and thereafter emulsifying the ground fish, meat and meat analog products. The emulsified fish or meat is then mixed with sodium chloride at from 0.5–3% sodium chloride based on the weight of the fabricated product. Following emulsification and sodium chloride addition, mixing is continued and transglutaminase coupled soy protein is added while mixing continues. The addition of the transglutaminase coupled soy protein product acts to stiffen the fish, meat and meat analog product preparatory to its being formed into chunks.

The transglutaminase coupled soy protein allows forming of the fish, meat and meat analog product into a chunk form by providing structural rigidity to the formed chunks. The skeletal matrix of the transglutaminase coupled soy protein also provides surfaces for protein gelatinaceous binding and helps form the internal rigid structure for the chunks to be formed thereafter. The transglutaminase coupled soy protein also extends the yield of the fish, meat and meat analog products through the subsequent blanching and cooking steps. After mixing with the transglutaminase coupled soy protein, a mass is formed, desirably into chunks, to resemble whole fish or meat chunks. The chunks are then heated in a water bath, known as blanching. At the blanching temperature the salt soluble protein is gelatinized, preferably within the transglutaminase coupled soy protein backbone structure. The gelatinized protein in the formed chunks of fish, meat and meat analog products cause setting or stiffening of the formed chunks of fabricated products.

The set chunks of fabricated fish, meat and meat analog products may then be admixed with other fish, meat and meat analog products, for example chunks of fish or meat, thereby extending the quantity of such fish, meat and meat analog products.

The final product is a relatively firm composition which possesses texturized qualities similar to whole chunks of meat and meat analog products.

The fish, meat and meat analog products used to prepare the fabricated chunks herein may include the usual fish, meat and meat analog products derived from fish houses and slaughterhouses. In addition, the whole carcass of horsemeat, lamb, beef, pork and chicken may be ground and emulsified as the meat and meat analog products.

Fat may also be separately added. However, a high fat content has an adverse effect on the binding properties of the fish, meat and meat analog products. Quite often in the processing of fish, meat and meat analogs, egg whites are added. The egg whites function as a binding agent. By employing a transglutaminase coupled soy protein, the use of egg whites as the binding agent is eliminated. This is due to the skeletal matrix of the transglutaminase coupled soy protein.

In the preferred embodiment of the process for making fabricated fish, meat and meat analog products chunks, frozen fish or meat and meat analog products, at a temperature of about 32° F. are ground in commercial grinders and then emulsified. The temperature of the emulsified fish, meat and meat analog products may rise to approximately 53° F. Water/ice, is added during the grinding and emulsification steps.

Thereafter the fish or meat is conveyed to a mixing vessel where the salt is added and mixing is permitted to continue for several minutes, usually approximately 3–8 minutes. During the mixing time the temperature rises and the salt solution extracts and solubilizes the necessary proteins from the fish, meat and meat analog products.

After sufficient mixing to assure protein extraction and solubilization, the protein-salt solution and emulsified fish or meat mass is further mixed while the transglutaminase coupled soy protein is added thereto. Mixing continues until the transglutaminase coupled soy protein has been uniformly distributed throughout the mass. Generally, this is accomplished within an additional 3–8 minutes. As stated above the transglutaminase coupled soy protein provides the matrix or surface on which the fish or meat protein is gelatinized during the subsequent blanching process and thereby serves to give structural rigidity to the fabricated fish, meat and meat analog products.

The meat or fish and the transglutaminase coupled soy protein mass is thereafter formed into small chunks in equipment used to form the chunk products. Chunks may be formed in a cylindrical shape of approximately ⅞ inch diameter by 1 inch in height. The temperature of the chunk mass when it exits the forming machine is about 53° F.

Thereafter, the chunks are placed in a blancher where the temperature of the water is maintained in the range of 170–210° F. for approximately 3–6 minutes. The optimum temperature is about 200–210° F. The higher the temperature the shorter the residence time required. In the blancher the protein is gelatinized or set thereby providing structural rigidity to the formed chunks. The set chunks are permitted to cool and thereafter may be used as a component of food products such as by combination with other fish, meat and meat analog products in chunk or other forms. Thereafter, the product may be cooked and packaged, and marketed and used as a food.

The need for structure enhancing protein in most commercialized applications is not necessary since the use of the muscle fraction of fish or meat is extensive and the availability of soluble protein is not limited. However, in the preferred embodiment of this invention fish, meat and meat analog products having limited amounts of soluble protein are advantageously used without other binding agents, and therefore it is economically necessary to extract the protein fraction described in order to maximize the availability of the proteins and provide the chunk fish or meat characteristic structural qualities in the fabricated fish, meat and meat analog products of this invention.

The chunk fabricated fish, meat and meat analog products resemble the relatively rigid structural composition and textured qualities similar to whole chunk fish and meat.

In the fabricated fish, meat and meat analog products, the binding characteristics are dependent upon the amount and size of the fat globule in relation to the protein available, and the moisture present and somewhat by the emulsion temperature of the fish or meat. Large fat globules inhibit the surrounding protein while the smaller globules increase the surface area subsequently diluting protein gel strength. Increased proportions of fat also tend to have an adverse effect on the fabricated fish, meat and meat analog product, particularly when a structurally rigid formed meat and meat analog product is required. Larger amounts of fat, particularly at high temperatures, tend to cause the fat to smear and prevent its incorporation into the proteinaceous gelatin. Generally, the fat-containing emulsified fish, meat and meat analog product should not be permitted to rise beyond about 90° F. through the forming step, and the preferred maximum temperature is in the range of 35–50° F. with about 44° F. being the most desired temperature. At temperatures within the preferred temperature range the adverse smearing effects of the fat are minimized.

In the preferred temperature of between about 35–50° F. maximum protein is extracted during the salt extraction step. Within this temperature range minimal protein is denatured permitting a good blend of the salt solubilized protein, emulsified fish or meat and the transglutaminase coupled soy protein.

During the blanching step, however, when the protein is denatured to form the gelatinaceous mass, the preferred temperature range is 170–210° F.

The moisture content of the fabricated fish, meat and meat analog product made by the process herein is maintained at about 70% or less. Excessive moisture thins the consistency of the emulsion mixture and has an adverse effect upon the subsequent forming step in that the high moisture content of the fabricated fish, meat and meat analog product tends to reduce the ability of the product to maintain a structurally rigid shape after being formed. Water in the fish, meat or meat analog product is usually sufficient to meet the stated water content range.

An example of a fish product containing the transglutaminase coupled soy protein of this invention is a "surimi dog,"

a hot dog made of fish. Surimi means "formed fish" and refers to fish pulp that is formed into various shapes. Surimi and the similar kamaboko have been made for centuries by the Japanese and are thought to date as far back as 1100 AD. Most surimi found in North America is made from Alaska pollock, a fish with a lean, firm flesh that has a delicate, slightly sweet flavor. Pacific whiting is also beginning to be used for surimi but its flesh is so soft that it requires the addition of egg whites and potatoes to be firm enough for processing. To become surimi, fish is skinned, boned, repeatedly rinsed to eliminate any fishiness and pigment and ground into a paste. This odorless white paste is then mixed with a flavor concentrate made from real shellfish, the solution from boiled shells or artificial flavorings. The paste is then formed, cooked and cut into the various shapes of the seafood it is imitating, which in the United States is usually crab legs, lobster chunks, shrimp and scallops. Lastly surimi is colored to complete its transformation from fish to shellfish look-alike.

Other ingredients may be added during the process of preparing the fabricated fish, meat and meat analog product, including soy flour, water sufficient to raise the moisture content to about 65%, dried egg powder, other fish or meat protein derivatives, egg albumen and food color.

A surimi dog composition utilizing a transglutaminase coupled soy protein is outlined below. The weight ratio of surimi:transglutaminase coupled soy protein emulsion is generally 2.5–3.5:1, preferably 2.75–3.25:1 and most preferably 3.0–3.15:1. The remaining components are adjusted accordingly. In the below Table III, all parts are by weight.

TABLE III

Preparation of a Surimi Dog

| Component | Parts by Weight |
|---|---|
| Surimi | 50.0 |
| Product of Example 1 Emulsion | 17.0 |
| Water/ice | 24.3 |
| Potato Starch | 5.0 |
| Salt | 1.8 |
| Sugar | 0.8 |
| Dextrose | 0.8 |
| MSG | 0.3 |

The Product of Example 1 Emulsion is prepared by mixing together 17.550 parts of the Product of Example 1 with 8.77 parts vegetable oil and 73.680 parts water/ice and blended to obtain an emulsion. The surimi dog is prepared by adding to a chilled mixer the following: the Product of Example 1 Emulsion and chopped surimi while maintaining the temperature at 0C. Salt is added and mixing is continued for 3 minutes. The water/ice is added and mixing is continued for an additional 6 minutes, at which time is added the starch, sugar, dextrose and MSG and mixing continued for 2 additional minutes. The contents are stuffed into casings to form the surimi dog.

The hardness in grams/force and the elasticity of a surimi dog made with transglutaminase coupled soy proteins prepared by the process described in this invention and a surimi dog made with a standard (non-transglutaminase coupled) soy protein are determined. The comparison is shown in Table IV below. The amount of transglutaminase per gram protein utilized in the coupling is either 0.3 or 0.6 units and the reaction time is either 30 or 50 minutes. The hardness and elasticity are measured on an Instron Two Cycle TPA. The hardness is measured by compressing a one inch sample of each surimi dog with a plate until the meat emulsion breaks. The breaking point is the hardness value and it indicates the firmness of the meat emulsion. In Table IV, all the surimi dogs made with the transglutaminase coupled soy protein have an improved hardness over the hardness of the control sample surimi dog. The elasticity is measured by the distance a probe goes into the sample before fracturing and is represented as a percent of sample height. Elasticity indicates the "bounce" of the teeth on the sample. In Table IV, all the surimi dogs made with the transglutaminase coupled soy protein have an improved hardness and elasticity over the hardness and elasticity of the control sample surimi dog.

TABLE IV

Evaluation of Surimi Dogs

| Sample | Hardness | Elasticity |
|---|---|---|
| Control | 310 | 8681 |
| 0.3 units TG/gram protein for 30 min. | 341 | 9370 |
| 0.3 units TG/gram protein for 50 min. | 357 | 9531 |
| 0.6 units TG/gram protein for 30 min. | 365 | 9739 |
| 0.6 units TG/gram protein for 50 min. | 368 | 9935 |

Vegetarian franks are also prepared using the transglutaminase coupled soy protein. A parts by weight (pbw) range of several of the components in the vegetarian franks during processing are as follows: transglutaminase coupled soy protein 10–15 pbw; vegetable oil 12–20 pbw; vital wheat gluten 2.5–4.5 pbw; and egg albumin 3–4 pbw. Other processing components are water/ice, liquid carmine, liquid smoke, lactose and seasonings.

The vegetarian franks are prepared by adding to a chilled mixer the product of Example 1 and the water/ice and mixed until the Example 1 product is fully hydrated. Vegetable oil is slowly added and mixing is continued until an emulsion is formed. Then added are the vital wheat gluten, egg albumin and liquid carmine and mixing is continued at high speed until the viscosity of the mixture reduces and the mixture becomes gluttonous. Mixing speed is reduced and added are the seasoning and the liquid smoke. Mixing is continued until the contents of the mixture are well dispersed. The mixture is stuffed into casings to form the vegetarian franks.

The hardness of vegetarian franks, either with a non-transglutaminase coupled soy protein plus egg whites (control) or with a transglutaminase coupled soy protein as both a protein source and binder (TG)are determined. As stated above, the transglutaminase coupled soy protein serves as a replacement of egg whites, which functions as a binding agent. The control sample vegetarian frank and the transglutaminase coupled soy protein vegetarian frank are cooked. The hardness of each sample after cooking is determined at both a cold temperature of 10–20° C. and a hot temperature of 80–90° C. The results are reported in Table V. At both temperature ratings, it is observed that the frank with the transglutaminase coupled soy protein has an improved hardness.

TABLE V

Vegetarian Franks
Warm and Cold Hardness

| Sample | Temperature | Hardness |
|---|---|---|
| Control | Cold | 5442 |
| TG | Cold | 6146 |
| Control | Hot | 3040 |
| TG | Hot | 5279 |

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A process for producing a transglutaminase coupled vegetable protein composition, comprising;

providing a vegetable protein extract;

forming a reaction mixture by adding to the vegetable extract an amount of transglutaminase that is sufficient to catalyze an acyl transfer reaction of a gamma-carboxamide group of a glutamine residue and a lysine residue in a peptide chain of the vegetable protein in the extract;

maintaining the reaction mixture at a sufficient temperature for a period of time sufficient to achieve a partially cross-linked vegetable protein;

acid precipitating the partially cross-linked vegetable protein;

removing the transglutaminase;

adjusting the pH to 7;

pasteurizing the partially cross-linked vegetable protein; and drying the partially cross-linked vegetable protein to form a powdered coupled vegetable protein composition.

2. The process of claim 1 wherein the vegetable protein extract is a soy protein extract.

3. The process of claim 1 wherein the amount of transglutaminase is utilized at a concentration of from 0.15 to 0.80 units transglutaminase per gram protein.

4. The process of claim 1 wherein the amount of transglutaminase is utilized at a concentration of from 0.25 to 0.65 units transglutaminase per gram protein.

5. The process of claim 1 wherein the vegetable protein extract has a total solids content of less than 6%.

6. The process of claim 1 wherein the vegetable protein extract has a total solids content of from about 3% to about 5%.

7. The process of claim 1 wherein the temperature of the reaction mixture is from about 40° C. to about 60° C.

8. The process of claim 1 wherein the temperature of the reaction mixture is about 50° C.

9. The process of claim 1 wherein the period of time is from about 10 minutes to about 60 minutes.

10. The process of claim 1 wherein pasteurizing takes place at a temperature of at least 265° F.

11. The process of claim 1 wherein pasteurizing takes place at a temperature of less than 310° F.

12. The process of claim 1 wherein while pasteurizing there is a % solids content of from 8–11.5%.

13. The process of claim 1 wherein while pasteurizing there is a % solids content of from 9–10%.

14. The process of claim 1 wherein drying is performed in a spray dryer.

15. The process of claim 14 wherein the spray dryer has an inlet temperature of from 400–450° F. and an outlet temperature of from 150–250° F.

16. The process of claim 1 wherein the coupled vegetable protein composition has a controlled salt sensitivity of from −30% to +30%.

17. The process of claim 1 wherein the coupled vegetable protein composition has a controlled salt sensitivity of from 0 to +20%.

18. The process for utilizing a transglutaminase coupled vegetable protein composition prepared according to the process of claim 1, comprising;

providing a fish, meat or meat analog product;

reducing the size of fish, meat or meat analog product;

emulsifying the reduced fish, meat or meat analog products with vegetable oil and water and ice;

mixing the emulsified fish, meat or meat analog product with sodium chloride; and adding the transglutaminase coupled vegetable protein to the fish meat or meat analog product to form a fabricated food for human consumption.

19. The process of claim 18 wherein the fabricated food is a fish product.

20. The process of claim 18 wherein the fabricated food is a meat product.

21. The process of claim 18 wherein the meat is selected from the group consisting of horsemeat, lamb, beef, pork and chicken.

22. The process of claim 18 wherein the fabricated food is a meat analog product.

* * * * *